US012752095B2

(12) United States Patent
Jiang et al.

(10) Patent No.: US 12,752,095 B2
(45) Date of Patent: Oct. 6, 2026

(54) UNIVERSAL SINGLE-USE CAP FOR MALE AND FEMALE CONNECTORS

(71) Applicant: Becton, Dickinson and Company, Franklin Lakes, NJ (US)

(72) Inventors: Chang Jiang, Butler, NJ (US); Nichola Charles, Budd Lake, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 963 days.

(21) Appl. No.: 17/045,841

(22) PCT Filed: Apr. 9, 2019

(86) PCT No.: PCT/US2019/026538
§ 371 (c)(1),
(2) Date: Oct. 7, 2020

(87) PCT Pub. No.: WO2019/199789
PCT Pub. Date: Oct. 17, 2019

(65) Prior Publication Data

US 2021/0138225 A1 May 13, 2021

Related U.S. Application Data

(60) Provisional application No. 62/655,526, filed on Apr. 10, 2018.

(51) Int. Cl.

| | |
|---|---|
| ***A61M 39/16*** | (2006.01) |
| ***A61M 39/20*** | (2006.01) |
| *A61M 39/22* | (2006.01) |

(52) U.S. Cl.
CPC ........ *A61M 39/165* (2013.01); *A61M 39/162* (2013.01); *A61M 39/20* (2013.01);
(Continued)

(58) Field of Classification Search
CPC .. A61M 39/165; A61M 39/162; A61M 39/20; A61M 2039/229;
(Continued)

(56) References Cited

U.S. PATENT DOCUMENTS

| | | | | |
|---|---|---|---|---|
| 8,628,501 B2 * | 1/2014 | Hadden | ............... | A61M 39/162 604/199 |
| 2010/0050351 A1 * | 3/2010 | Colantonio | ............... | B08B 1/14 15/104.93 |

(Continued)

FOREIGN PATENT DOCUMENTS

| | | | | |
|---|---|---|---|---|
| WO | 2013192574 A1 | 12/2013 | | |
| WO | WO-2015174953 A1 * | 11/2015 | ............ | A61M 25/00 |
| WO | 2017127364 A1 | 7/2017 | | |

OTHER PUBLICATIONS

PCT International Search Report and Written Opinion in PCT/US2019/026538 dated Jul. 26, 2019, 12 pages.

*Primary Examiner* — Michael J Tsai
*Assistant Examiner* — Neeraja Gollamudi
(74) *Attorney, Agent, or Firm* — Servilla Whitney LLC

(57) ABSTRACT

A device for connection to a medical connector, the device includes a cap, an elastic sealing ring and a peelable seal. The cap configured to define a chamber to contain an absorbent material and disinfectant or antimicrobial agent. The cap includes one or more threads adapted to engage with a female luer connector. The cap is adapted to engage a male luer connector in a press-fit connection. The peelable seal prevents the disinfectant or the antimicrobial agent from exiting the chamber.

20 Claims, 9 Drawing Sheets

(52) U.S. Cl.
CPC ................. *A61M 2039/229* (2013.01); *A61M 2205/0216* (2013.01)

(58) Field of Classification Search
CPC .. A61M 2205/0216; A61M 2039/0285; A61M 2039/1066; A61M 2039/0288
See application file for complete search history.

(56) References Cited

U.S. PATENT DOCUMENTS

| | | | | |
|---|---|---|---|---|
| 2011/0044850 | A1* | 2/2011 | Solomon ............. | A61M 39/165 422/292 |
| 2011/0125104 | A1 | 5/2011 | Lynn | |
| 2013/0030414 | A1* | 1/2013 | Gardner ................ | A61M 39/20 604/533 |
| 2016/0144118 | A1* | 5/2016 | Solomon ................. | A61M 5/30 206/370 |
| 2016/0213912 | A1* | 7/2016 | Daneluzzi ........... | A61M 39/165 |
| 2017/0050013 | A1* | 2/2017 | Bedoe ................... | A61M 39/20 |
| 2017/0203092 | A1* | 7/2017 | Ryan ................... | A61M 39/162 |
| 2017/0232121 | A1* | 8/2017 | Chiu ...................... | A61B 90/70 422/28 |
| 2021/0138224 | A1* | 5/2021 | Marici ................ | A61M 39/165 |

* cited by examiner

UNIVERSAL SINGLE-USE CAP FOR MALE AND FEMALE CONNECTORS

CROSS-REFERENCE TO RELATED APPLICATIONS

This application is the national stage entry of PCT/US2019/026538, filed on Apr. 9, 2019, which claims priority from provisional U.S. Patent Application No. 62/655,526 filed Apr. 10, 2018, the disclosures of which are hereby incorporated by reference in their entirety.

TECHNICAL FIELD

The present disclosure generally relates to a device for disinfecting and sterilizing access ports with, e.g., male and female luer fitting, and, in particular, to disinfecting and sterilizing devices capable of accommodating multiple types of connectors.

BACKGROUND

Vascular access devices (VAD's) are commonly used therapeutic devices and include intravenous (IV) catheters. There are two general classifications of VAD's, peripheral catheters and central venous catheters. Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures.

Disinfection caps have been added to the Society for Healthcare Epidemiology of America (SHEA) guidelines and early indications are that caps will also be incorporated into the 2016 Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Currently, caps for male needleless connectors, female needleless connectors, intravenous (IV), and hemodialysis lines use different designs and are therefore limited to the types of connectors to which the cap can be attached. Thus, prior disinfecting caps were designed to fit one type of connector only, and were specific to one particular size and/or shape of connector. Thus, there is a need for a disinfecting device capable of accommodating multiple types of connectors to streamline the disinfecting process. There is also a need for a disinfecting device capable of continuous disinfection for multiple days.

SUMMARY

One aspect of the present disclosure pertains to a device for connection to a medical connector. According to an exemplary embodiment of the present disclosure, the device generally comprises a cap, an elastic sealing ring, absorbent material, a disinfectant or the antimicrobial agent and a peelable seal. The cap comprises an integral body, a closed end, an annular wall having a length extending from the closed end to an open end that defines a chamber containing an absorbent material and disinfectant or antimicrobial agent. The open end defines an end face and includes a peripheral ledge extending radially inward from the annular wall. The open end defines an engagement surface.

The annular wall of the cap comprises an exterior wall surface and an interior wall surface. The interior wall surface defines an opening adjacent to the open end.

The elastic sealing ring comprises a dilatable opening therethrough sized and adapted to receive a male luer connector, a female luer connector and a hemodialysis connector. The dilatable opening can be sized to frictionally engage a male luer connector or female luer connector with a compatible diameter.

In one or more embodiments, the dilatable opening has a diameter that is dilatable from an initial diameter in a range from about 7-9 mm to a dilated diameter in a range from about 9-12 mm. In one or more embodiments, the elastic sealing ring is in contact with the peripheral ledge. In one or more embodiments, the male luer connector frictionally engages the dilatable opening via a press-fit connection upon insertion into the chamber through the dilatable opening of the elastic sealing ring.

In one or more embodiments, the opening adjacent to the open end of the interior wall surface is sized and adapted to receive an elastic sealing ring in a press-fit connection.

The interior wall surface comprises internal threads adjacent to the closed end. The internal threads are adapted and sized to engage a female luer connector. In one or more embodiments, the internal threads adjacent the closed end of the cap partially extend along a length of the interior wall surface of the cap.

The absorbent material and the disinfectant or the antimicrobial agent contacts the male luer connector, the female luer connector and the hemodialysis connector after insertion of the connector through the dilatable opening of the elastic sealing ring.

The peelable seal is disposed on the end face of the cap to prevent the disinfectant or the antimicrobial agent from exiting the chamber.

In one or more embodiments, the female luer connector is selected from the group consisting of needle-free connectors, stopcocks, and hemodialysis connectors.

In one or more embodiments, the male connector is an intravenous tubing end or stopcock.

In one or more embodiments, the male luer connector rests on the peripheral ledge upon being fully inserted in into the chamber.

In one or more embodiments, the male luer connector frictionally engages the interior wall surface via a press-fit connection upon insertion into the chamber.

In one or more embodiments, the opening adjacent the open end of the interior wall surface of the cap is sized and adapted to receive a male luer connector in a press-fit connection.

The elastic sealing ring comprises an elastomeric material.

In one or more embodiments, the elastomeric material of the elastic sealing ring comprises a thermoplastic elastomer.

In one or more embodiments, the chamber comprises a first portion adjacent to the closed end having a first portion diameter and a second portion adjacent to the open end having a second portion diameter, the first portion and second portion in fluid communication with each other and the first portion diameter being less than the second portion diameter. In one or more embodiments, the annular wall of the cap is frusto-conically shaped.

The cap is made from any of a number of types of plastic materials such as polycarbonate, polypropylene, polyethylene, glycol-modified polyethylene terephthalate, acrylonitrile butadiene styrene or any other moldable plastic material used in medical devices. In one or more embodiments, the cap comprises a polypropylene or polyethylene material. In one or more embodiments, the exterior cap surface includes a plurality of grip members.

In one or more embodiments, the absorbent material is under radial compression by the internal threads to retain the absorbent material in the chamber. In one or more embodiments, the absorbent material is retained in the chamber without radial compression by the internal threads. In one or more embodiments, the absorbent material is a nonwoven material, foam or a sponge. In a specific embodiment, the foam is a polyurethane foam.

In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material toward the closed end of the chamber upon connection to the female luer connector or the male luer connector allows the connector to contact the disinfectant or antimicrobial agent to disinfect the female luer connector or the male luer connector.

In one or more embodiments, the peelable seal comprises an aluminum or multi-layer polymer film peel back top. In a specific embodiment, the peelable seal is heat-sealed or induction sealed to the cap open end.

An alternate embodiment of the present disclosure pertains to a device for connection to a medical connector according to an exemplary embodiment of the present disclosure generally comprises a cap, an elastic sealing ring having one or more undercuts and a dilatable opening, absorbent material, a disinfectant or the antimicrobial agent and a peelable seal.

A second aspect of the present disclosure pertains to a method of disinfecting a medical connector. The method comprises connecting the device of one or more embodiments to a medical connector, wherein connecting includes engaging the interior wall surface upon insertion into the chamber such that the medical connector contacts the absorbent material and the disinfectant or antimicrobial agent.

A third aspect of the present disclosure pertains to an assembly. The assembly comprises the device of one or more embodiments connected to a medical connector. In one or more embodiments, the medical connector is selected from a male luer connector, a female luer connector, and needleless connector.

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

Embodiments of the disclosure pertain to a universal single-use device for connection to and disinfection of a medical connector, including male luer connectors and female luer connectors, in which the device comprises a cap, an elastic sealing ring, absorbent material, a disinfectant or the antimicrobial agent and a peelable seal. The device provides a mechanical barrier for connectors and contains an antimicrobial agent for disinfection. The device of the present disclosure allows the practitioner to streamline the disinfecting process.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

Figure 1:
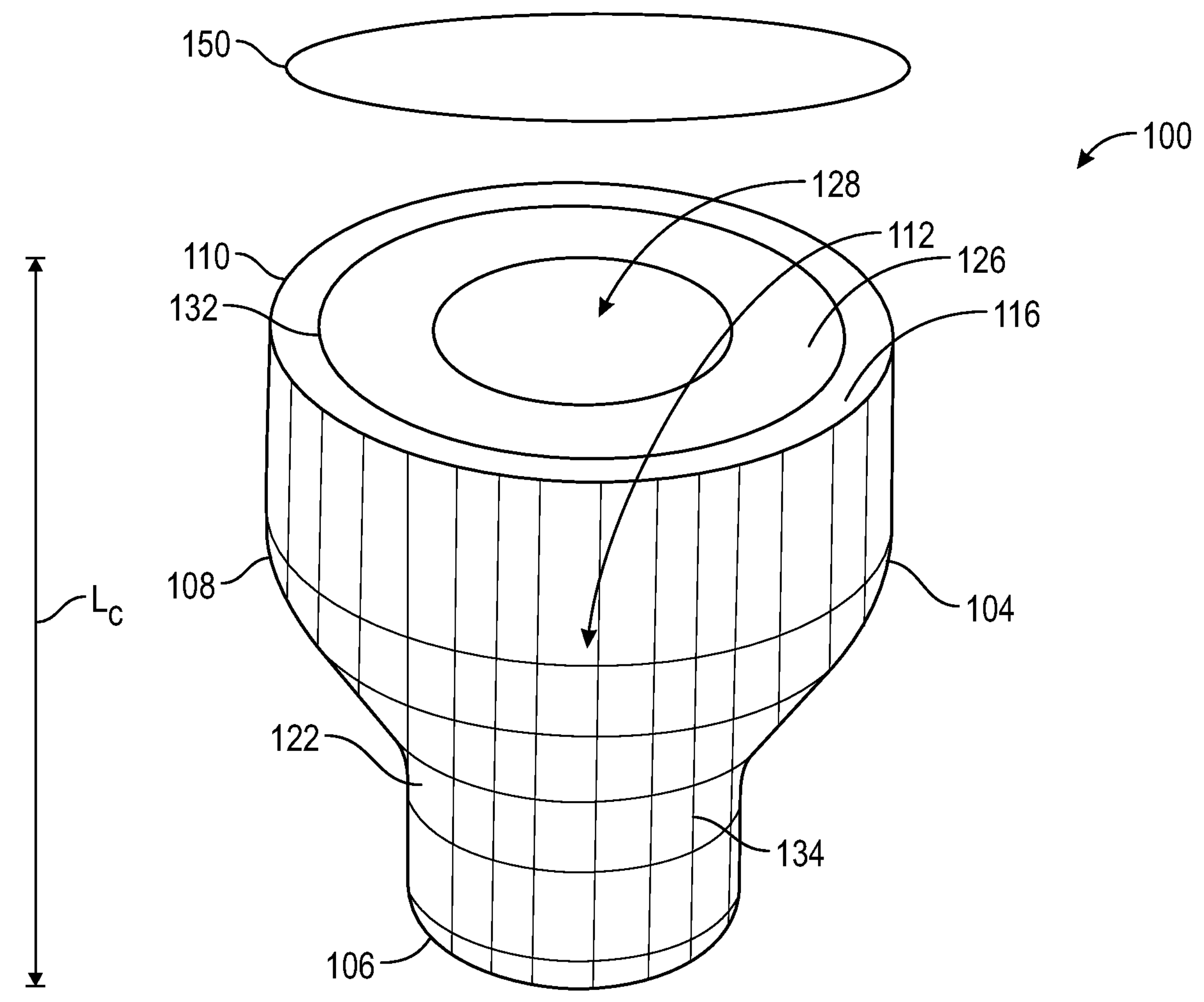
FIG. 1 shows a side elevation view of a device according to an embodiment of the present disclosure.
Figure 2:
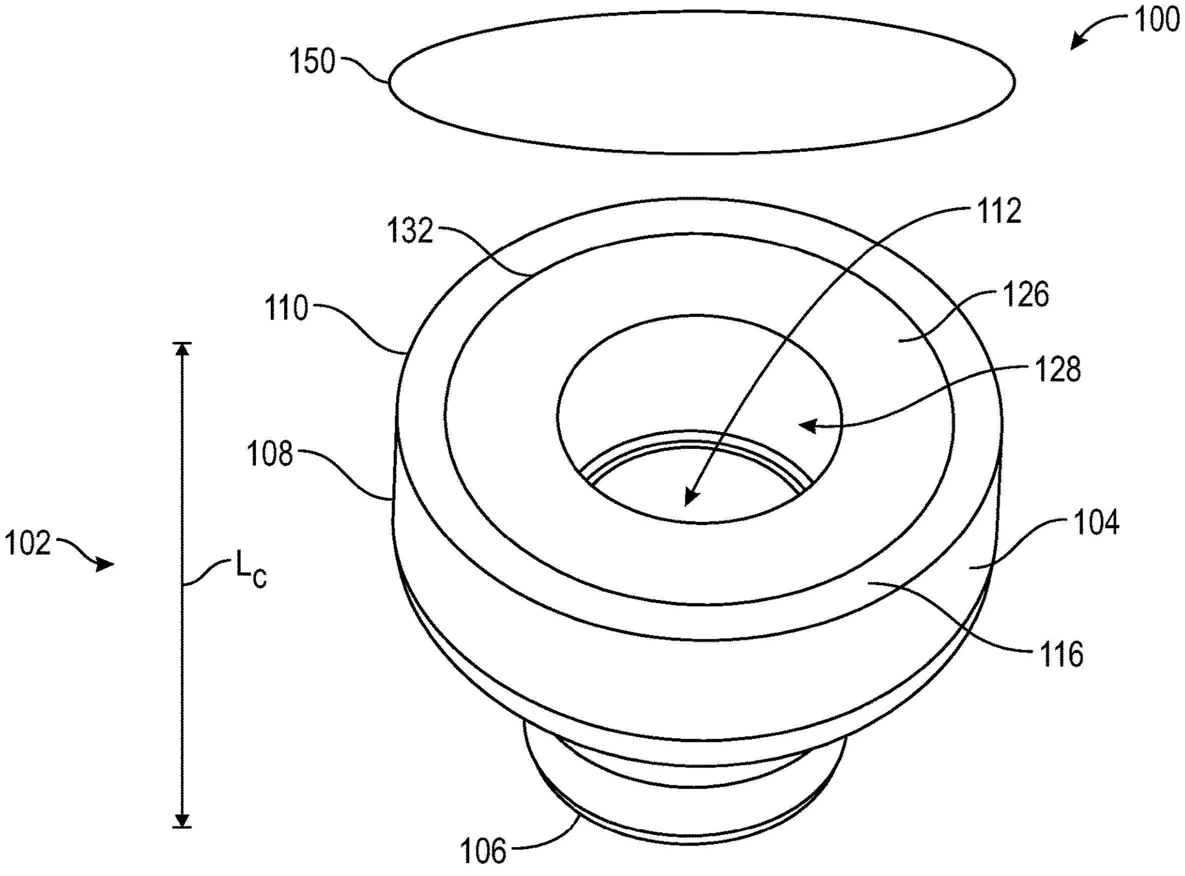
FIG. 2 shows a top perspective view of a device according to an embodiment of the present disclosure.
Figure 3:
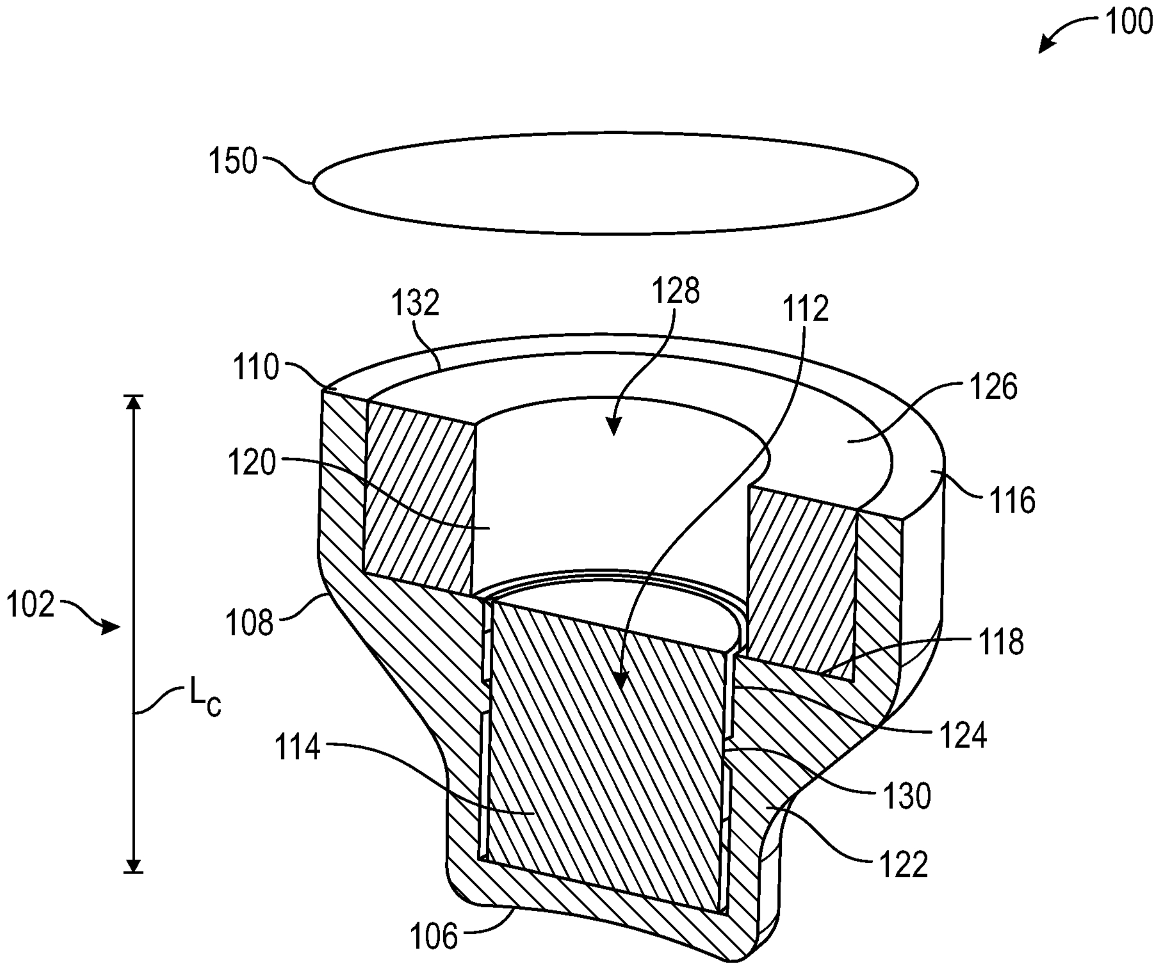
FIG. 3 shows a partial sectional view of the components of a device according to an embodiment of the present disclosure.
Figure 4:
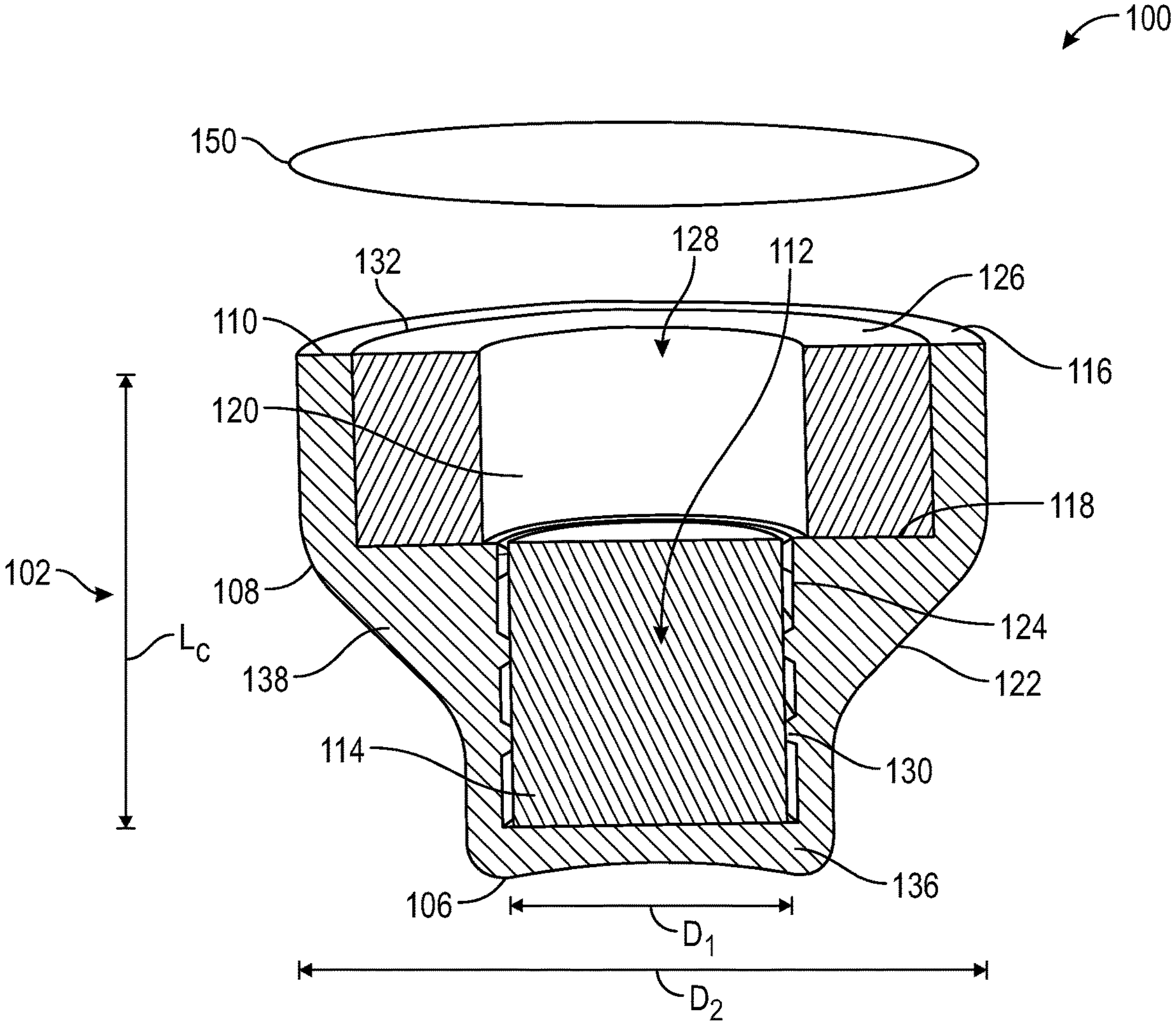
FIG. 4 shows a partial sectional view of the components of a device according to an embodiment of the present disclosure.
Figure 5:
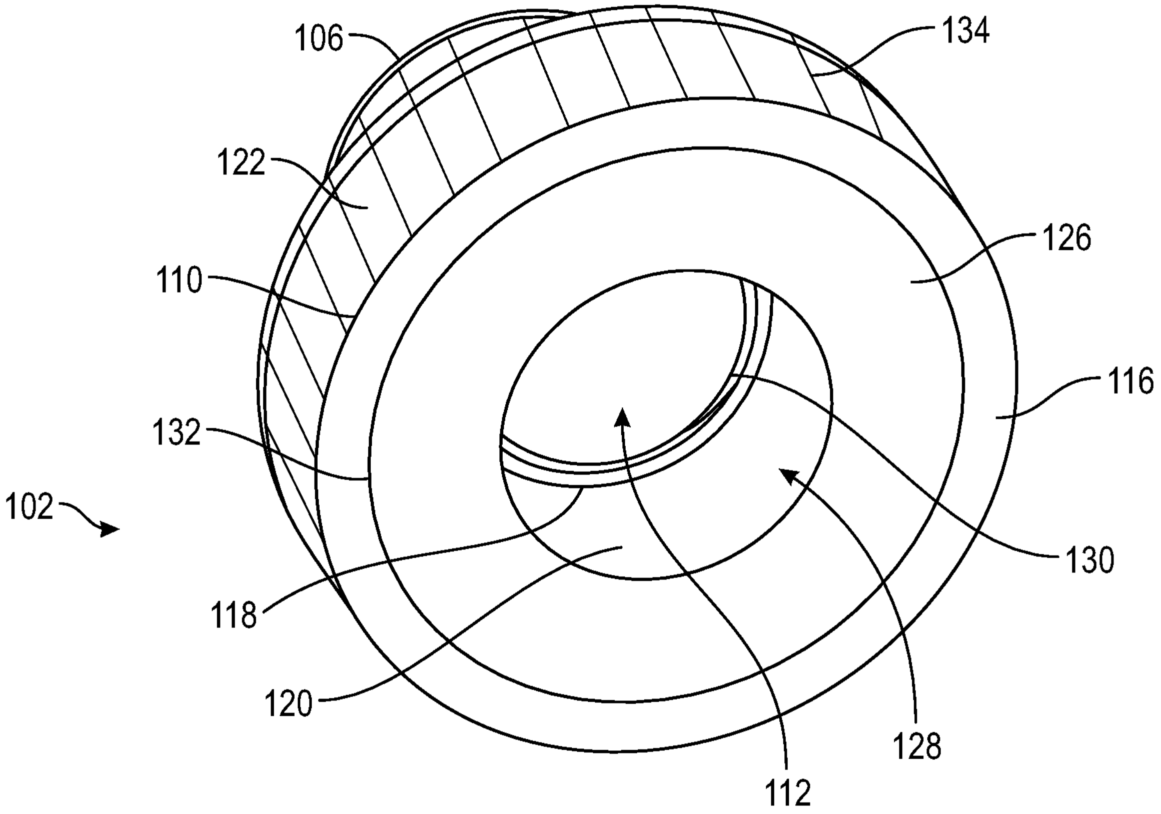
FIG. 5 shows a top view of a component of a device according to an embodiment of the present disclosure.
Figure 6:
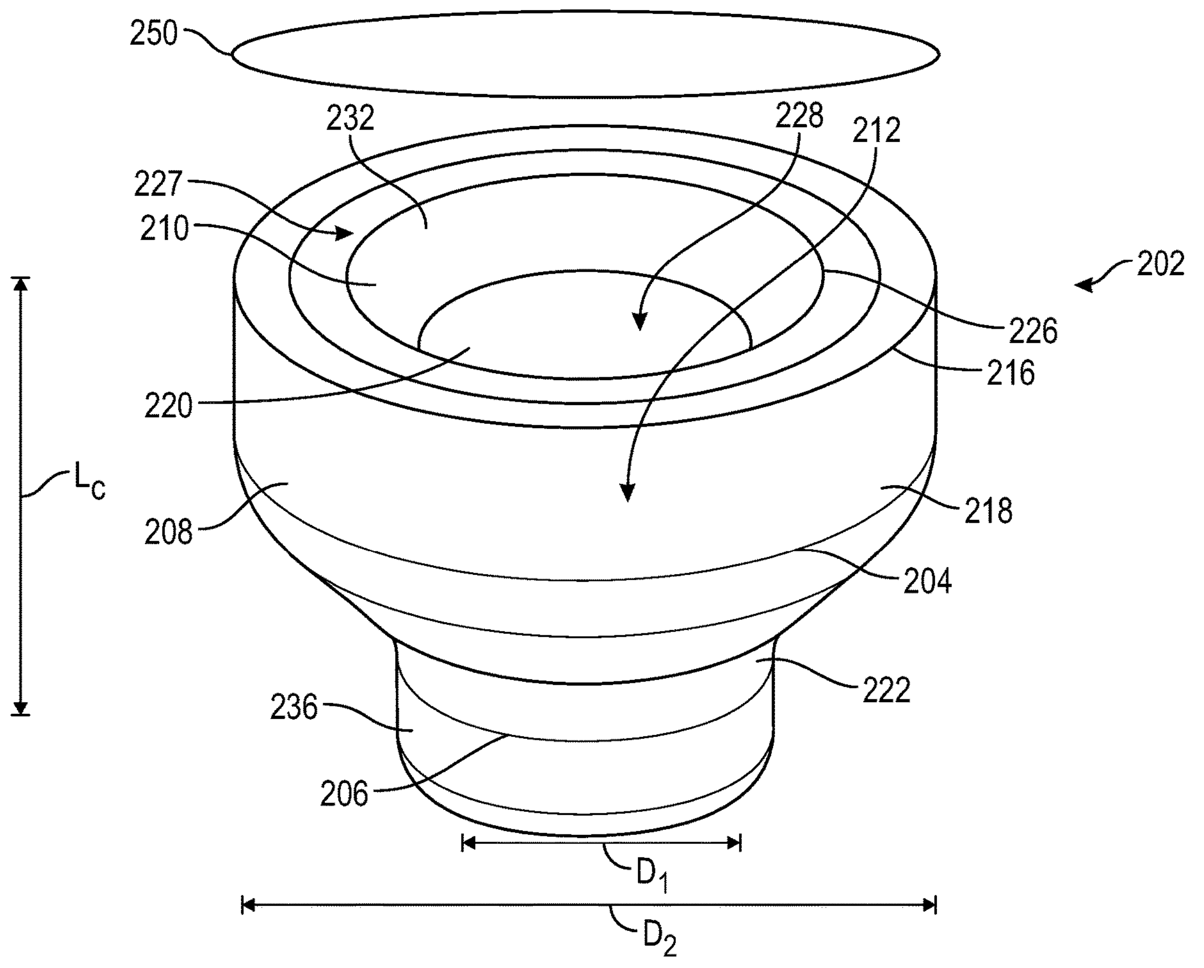
FIG. 6 shows a side elevation view of a device according to an alternate embodiment of the present disclosure.
Figure 7:
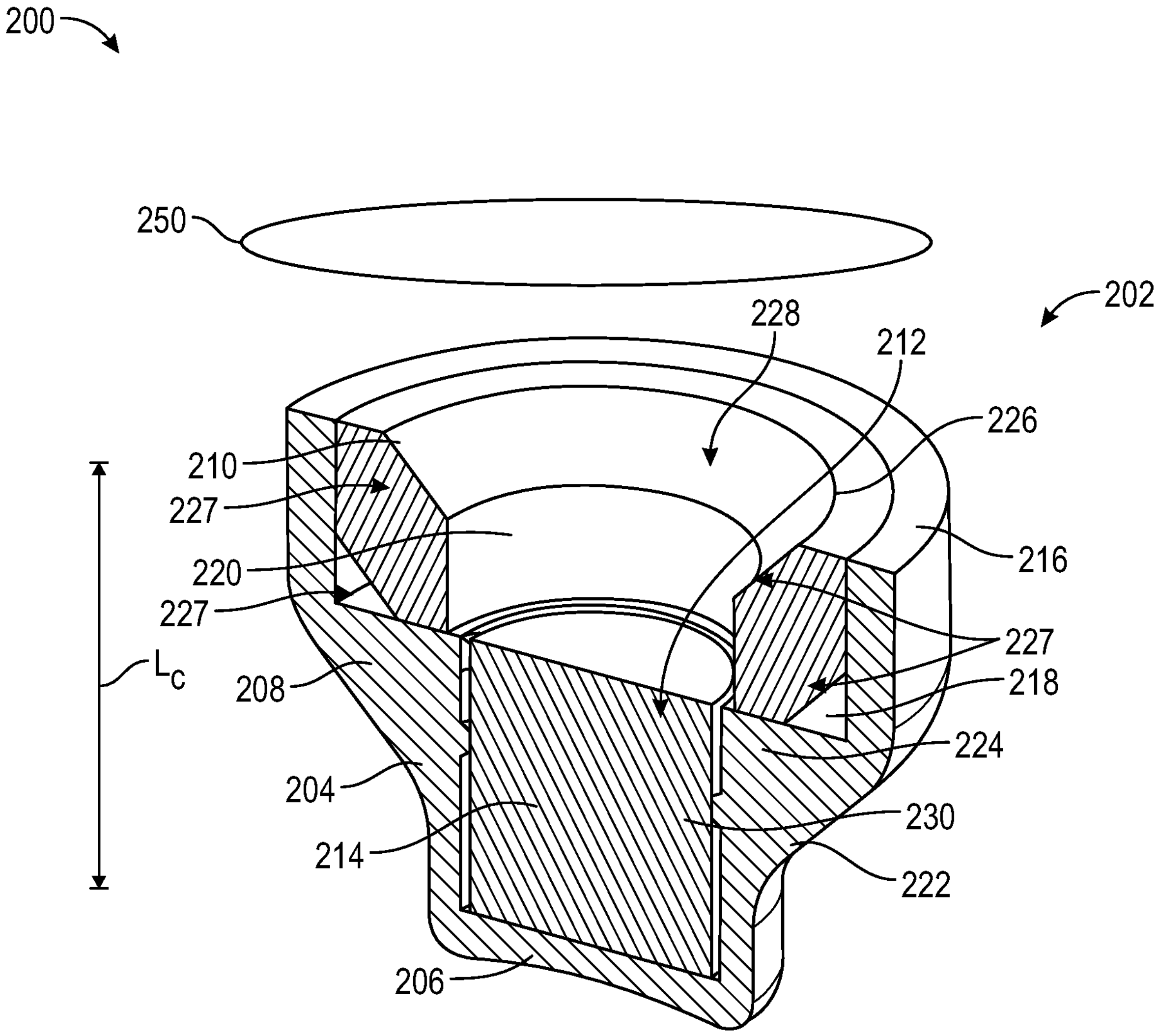
FIG. 7 shows a partial sectional view of the components of an alternate device according to an alternate embodiment of the present disclosure.
Figure 8:
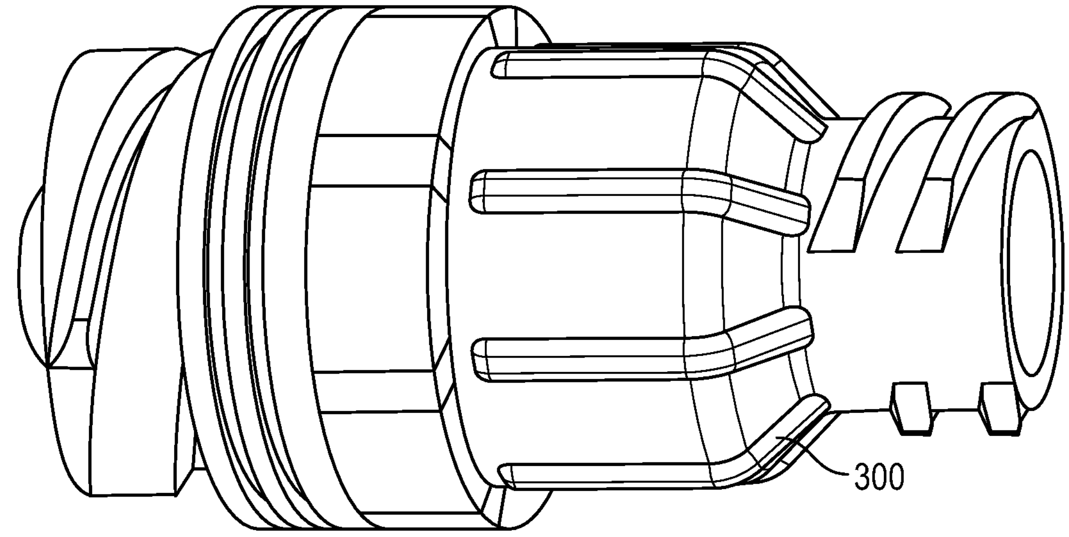
FIG. 8 (PRIOR ART)
FIG. 8 shows a perspective view of a female luer connector with septum according to the prior art.
Figure 9:
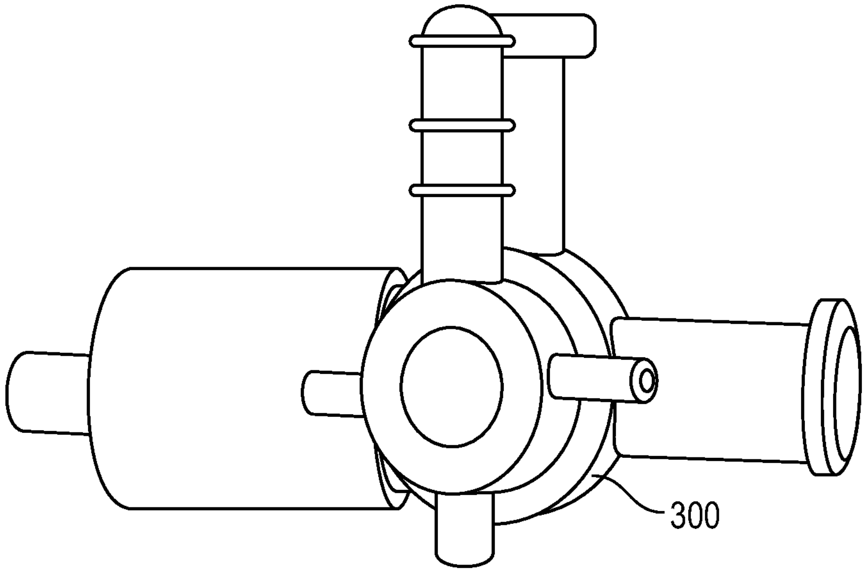
FIG. 9 (PRIOR ART)
FIG. 9 shows a perspective view a female luer connector with stopcock according to the prior art.
Figure 10:
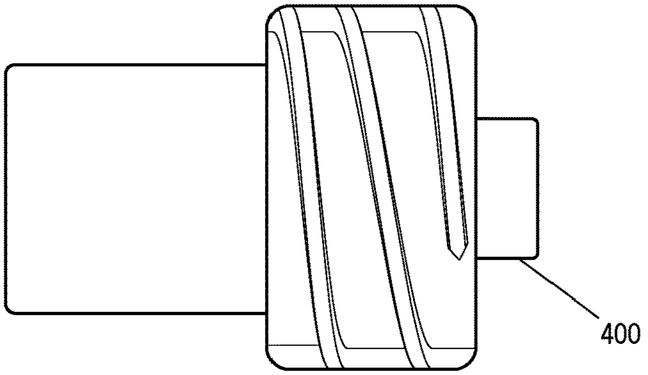
FIG. 10 (PRIOR ART)
FIG. 10 shows a perspective view of a male luer connector according to the prior art.
Figure 11:
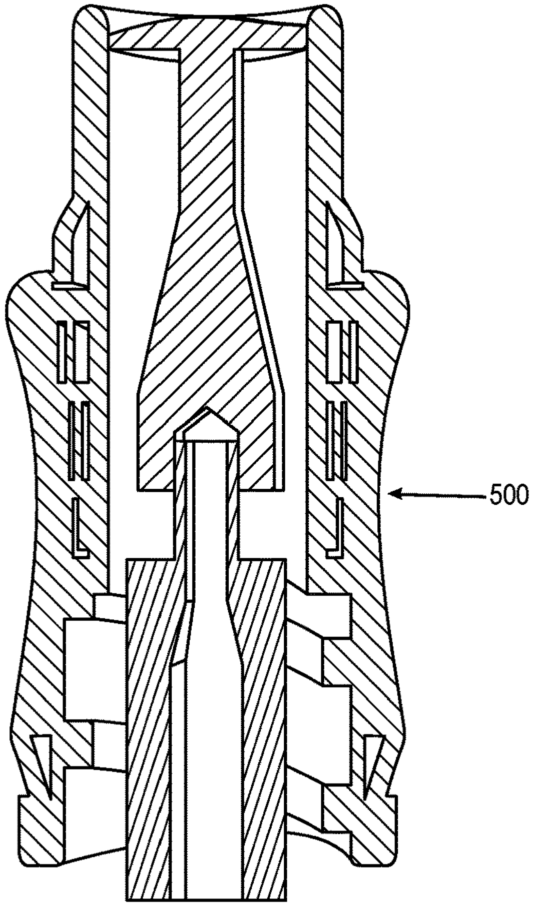
FIG. 11 (PRIOR ART)
FIG. 11 shows a perspective view of a hemodialysis connector according to the prior art.

The assembled device 100 according to one or more embodiments is shown in FIGS. 1-4. FIG. 5 shows the cap component of the device according to embodiments of the present disclosure. FIGS. 6 and 7 show a device and its components according to an alternate embodiment of the present disclosure. FIGS. 8 to 11 show various medical connectors according to the prior art. Referring to FIGS. 1-5, device 100 for connection to a medical connector according to an exemplary embodiment of the present disclosure generally comprises a cap 102, an elastic sealing ring 126, absorbent material 114, a disinfectant or an antimicrobial agent, and a peelable seal 150. The cap 102 comprises an integral body 104, a closed end 106, an annular wall 108 having a length $L_C$ extending from the closed end 106 to an open end 110 that defines a chamber 112 containing an absorbent material 114 and disinfectant or antimicrobial agent. The open end 110 defines an end face 116 and comprises a peripheral ledge 118 extending radially inward from the annular wall 108, the open end 110 also defines an engagement surface 120.

The annular wall 108 of the cap 102 comprises an exterior wall surface 122 and an interior wall surface 124. The interior wall surface 124 defines an opening 132 adjacent the open end 110.

The elastic sealing ring 126 comprises a dilatable opening 128 therethrough sized and adapted to receive a male luer connector, a female luer connector, and a hemodialysis connector. The dilatable opening 128 can be sized to frictionally engage a male luer connector or female luer connector with a compatible diameter. In one or more embodiments, the dilatable opening 128 has a diameter that is dilatable from an initial diameter in a range from about 7-9 mm to a dilated diameter in a range from about 9-12 mm. In one or more embodiments, the elastic sealing ring 126 is in contact with the peripheral ledge 118. In one or more embodiments, the male luer connector frictionally engages the dilatable opening 128 via a press-fit connection upon insertion into the chamber 112 through the dilatable opening 128 of the elastic sealing ring 126. In one or more embodiments, the elastic sealing ring 126 is in contact with the peripheral ledge 118.

In one or more embodiments, the opening 132 adjacent the open end 110 of the interior wall surface 124 is sized and adapted to receive an elastic sealing ring 126 in a press-fit connection.

The interior wall surface 124 comprises internal threads 130 adjacent to the closed end 106. The internal threads 130 are adapted and sized to engage a female luer connector. In one or more embodiments, the internal threads 130 adjacent the closed end 106 of the cap 102 partially extend along a length of the interior wall surface 124 of the cap 102.

The absorbent material 114 and the disinfectant or the antimicrobial agent contacts the male luer connector, the female luer connector, and the hemodialysis connector after insertion of the connector through the dilatable opening 128 of the elastic sealing ring 126.

The peelable seal 150 is disposed on the end face 116 of the cap 102 to prevent the disinfectant or the antimicrobial agent from exiting the chamber 112.

The interior wall surface 124 comprises internal threads 130 adjacent to the closed end 106. The internal threads 130 are adapted and sized to engage a female luer connector. The absorbent material 114 and the disinfectant or the antimicrobial agent contacts the male luer connector, the female luer connector, and the hemodialysis connector after insertion of the connector into the open end 110 of the cap 102.

In one or more embodiments, the exterior wall surface 122 of the cap 102 comprises a plurality of grip members 134.

The cap 102 comprises an annular cap wall 108 having a cap wall length $L_C$ extending from a cap closed end 106 to a cap open end 110. The cap 102 comprises an interior wall surface 124 and an exterior wall surface 122.

The peelable seal 150 is disposed on the cap open end 110 to prevent the disinfectant or the antimicrobial agent from exiting the chamber 112.

In one or more embodiments, the female connector may be selected from the group consisting of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end, stopcock or male lock luer.

In one or more embodiments, the male luer connector rests on the peripheral ledge 118 upon being fully inserted in into the chamber 112.

In one or more embodiments, the internal threads 130 adjacent the closed end 106 of the cap 102 partially extend along a length of the interior wall surface 124 of the cap 102.

In one or more embodiments, the male luer connector frictionally engages the interior wall surface 124 via a press-fit connection upon insertion into the chamber 112.

In one or more embodiments, the opening 132 adjacent the open end 110 of the interior wall surface 124 of the cap 102 is sized and adapted to receive a male luer connector in a press-fit connection.

The elastic sealing ring 126 comprises an elastomeric material.

In one or more embodiments, the elastomeric material of the elastic sealing ring 126 comprises a thermoplastic elastomer.

In one or more embodiments, the chamber 112 comprises a first portion 136 adjacent the closed end 106 having a first portion diameter $D_1$ and a second portion 138 adjacent the open end 110 having a second portion diameter $D_2$, the first portion 136 and second portion 138 in fluid communication with each other and the first portion diameter $D_1$ being less than the second portion diameter $D_2$. In one or more embodiments, the annular wall 108 of the cap 102 is frusto-conically shaped.

The cap 102 is made from any of a number of types of plastic materials such as polycarbonate, polypropylene, polyethylene, glycol-modified polyethylene terephthalate, acrylonitrile butadiene styrene or any other moldable plastic material used in medical devices. In one or more embodiments, the cap 102 comprises a polypropylene or polyethylene material. In one or more embodiments, the exterior wall surface 122 includes a plurality of grip members 134.

In one or more embodiments, the absorbent material 114 is under radial compression by the internal threads 130 to retain the absorbent material 114 in the chamber 112. In one or more embodiments, the absorbent material is retained in the chamber without radial compression by the internal threads. In one or more embodiments, the absorbent material 114 is a nonwoven material, foam, or a sponge. In a specific embodiment, the foam is a polyurethane foam. In a specific embodiment the absorbent material 114 is in the form of a foam plug.

The device 100 can achieve disinfection when used on luer connectors by integrating disinfectant or antimicrobial agent in the chamber 112 of the cap 102. The disinfectant or antimicrobial agent can be directly included in the chamber 112 or disinfectant or antimicrobial agent can be absorbed into sponges or foam material that fills the chamber 112 of the cap 102. The device 100 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 114 toward the closed end 106 of the chamber 112 upon connection to the female luer connector or the male luer connector allows the connector to contact the disinfectant or antimicrobial agent to disinfect the female luer connector or the male luer connector.

In one or embodiments, the peelable seal 150 may be placed on the end face 116 to prevent the disinfectant or the antimicrobial agent from exiting the chamber 112.

In one or more embodiments, the peelable seal 150 comprises an aluminum or multi-layer polymer film peel back top. In a specific embodiment, the peelable seal 150 is heat-sealed or induction sealed to the cap open end. In one or more embodiments, the peelable seal 150 comprises a moisture barrier.

In one or more embodiments, the cap exterior wall surface 122 includes a plurality of grip members 134.

Disinfecting caps currently on the market are capable of only disinfecting one of the three types of luer fitting, namely female luer of needle-free connectors, female luer of stopcocks, and male luer connectors on intravenous injection sites. Thus, to avoid having to use different types of disinfecting caps to clean different types of connectors, cap 102 engages with male luer connectors and also with female luer connectors, thereby allowing the user to clean different types of connectors with a single device. Upon mounting the cap 102 onto female luer connectors, the female luer connectors is inserted into the chamber 112 and screwed onto the internal threads 130 of the cap 102. Upon mounting the cap 102 onto a male luer connector, the male luer connector frictionally engages the interior wall surface 124 upon insertion into the chamber 112. Hence, the device 100 of the present disclosure can be mounted onto both male and female luer connectors thus fulfilling a current need in the art.

Another aspect of the present disclosure, as shown in FIGS. 6 and 7, relates to an assembled device 200 having an elastic sealing ring 226 that includes one or more cuts and/or tapered surfaces 227 providing improved adaptability to various types of connectors.

Referring to FIGS. 6 and 7, device 200 for connection to a medical connector according to an exemplary embodiment of the present disclosure generally comprises a cap 202, an elastic sealing ring 226 that includes one or more cuts and/or tapered surfaces 227, absorbent material 214, a disinfectant or an antimicrobial agent, and a peelable seal 250. The cap 202 comprises an integral body 204, a closed end 206, an annular wall 208 having a length $L_C$ extending from the closed end 206 to an open end 210 that defines a chamber 212 containing an absorbent material 214 and disinfectant or antimicrobial agent. The open end 210 defines an end face 216 and comprises a peripheral ledge 218 extending radially inward from the annular wall 208, the open end 210 also defines an engagement surface 220.

The annular wall 208 of the cap 202 comprises an exterior wall surface 222 and an interior wall surface 224. The interior wall surface 224 defines an opening 232 adjacent the open end 210.

The elastic sealing ring 226 comprises one or more cuts and/or tapered surfaces 227 providing improved adaptability to various types of connectors and a dilatable opening 228 therethrough sized and adapted to receive a male luer connector, a female luer connector, and a hemodialysis connector. The dilatable opening 228 can be sized to frictionally engage a male luer connector or female luer connector with a compatible diameter. In one or more embodiments, the dilatable opening 228 has a diameter that is dilatable from an initial diameter in a range from about 7-9 mm to a dilated diameter in a range from about 9-12 mm. In one or more embodiments, as shown in FIG. 7, the elastic sealing ring 226 is in contact with the peripheral ledge 218. In one or more embodiments, the male luer connector frictionally engages the dilatable opening 228 via a press-fit connection upon insertion into the chamber 212 through the dilatable opening 228 of the elastic sealing ring 226. In one or more embodiments, the elastic sealing ring 226 is in contact with the peripheral ledge 218.

In one or more embodiments, the opening 232 adjacent the open end 210 of the interior wall surface 224 is sized and adapted to receive an elastic sealing ring 226 in a press-fit connection. The elastic sealing ring 226 comprises one or more undercuts and/or tapered surfaces 227 providing improved adaptability to various types of connectors. As shown in FIG. 7, the one or more undercuts and/or tapered surfaces 227 may be placed on the surface of the elastic sealing ring 226 facing the dilatable opening 228. As shown in FIG. 7, the one or more undercuts and/or tapered surfaces 227 may be placed on the surface of the elastic sealing ring 226 facing the peripheral ledge 218.

The interior wall surface 224 comprises internal threads 230 adjacent to the closed end 206. The internal threads 230 are adapted and sized to engage a female luer connector. In one or more embodiments, the internal threads 230 adjacent the closed end 206 of the cap 202 partially extend along a length of the interior wall surface 224 of the cap 202.

The absorbent material 214 and the disinfectant or the antimicrobial agent contacts the male luer connector, the female luer connector, and the hemodialysis connector after insertion of the connector through the dilatable opening 228 of the elastic sealing ring 226.

The peelable seal 250 is disposed on the end face 216 of the cap 202 to prevent the disinfectant or the antimicrobial agent from exiting the chamber 212.

The interior wall surface 224 comprises internal threads 230 adjacent to the closed end 206. The internal threads 230 are adapted and sized to engage a female luer connector. The absorbent material 214 and the disinfectant or the antimicrobial agent contacts the male luer connector, the female luer connector, and the hemodialysis connector after insertion of the connector into the open end 210 of the cap 202.

In one or more embodiments, the exterior wall surface 222 of the cap 202 comprises a plurality of grip members.

The cap 202 comprises an annular cap wall 208 having a cap wall length $L_C$ extending from a cap closed end 206 to a cap open end 210. The cap 202 comprises an interior wall surface 224 and an exterior wall surface 222.

The peelable seal 250 is disposed on the cap open end 210 to prevent the disinfectant or the antimicrobial agent from exiting the chamber 212.

In one or more embodiments, the female connector may be selected from the group consisting of needle-free connectors, catheter luer connectors, stopcocks, and hemodialysis connectors.

In one or more embodiments, the male connector may be an intravenous tubing end, stopcock or male lock luer.

In one or more embodiments, the male luer connector rests on the peripheral ledge 218 upon being fully inserted in into the chamber 212.

In one or more embodiments, the internal threads 230 adjacent the closed end 206 of the cap 202 partially extend along a length of the interior wall surface 224 of the cap 202.

In one or more embodiments, the male luer connector frictionally engages the interior wall surface 224 via a press-fit connection upon insertion into the chamber 212.

In one or more embodiments, the opening 232 adjacent the open end 210 of the interior wall surface 224 of the cap 202 is sized and adapted to receive a male luer connector in a press-fit connection.

The elastic sealing ring 226 comprises an elastomeric material.

In one or more embodiments, the elastomeric material of the elastic sealing ring 226 comprises a thermoplastic elastomer.

In one or more embodiments, the chamber 212 comprises a first portion 236 adjacent the closed end 206 having a first portion diameter $D_1$ and a second portion 238 adjacent the open end 210 having a second portion diameter $D_2$, the first portion 236 and second portion 238 in fluid communication with each other and the first portion diameter $D_1$ being less than the second portion diameter $D_2$. In one or more embodiments, the annular wall 208 of the cap 202 is frusto-conically shaped.

The cap 202 is made from any of a number of types of plastic materials such as polycarbonate, polypropylene, polyethylene, glycol-modified polyethylene terephthalate, acrylonitrile butadiene styrene or any other moldable plastic material used in medical devices. In one or more embodiments, the cap 202 comprises a polypropylene or polyethylene material. In one or more embodiments, the exterior wall surface 222 includes a plurality of grip members.

In one or more embodiments, the absorbent material 214 is under radial compression by the internal threads 230 to retain the absorbent material 214 in the chamber 212. In one or more embodiments, the absorbent material is retained in the chamber without radial compression by the internal threads. In one or more embodiments, the absorbent material 214 is a nonwoven material, foam, or a sponge. In a specific embodiment, the foam is a polyurethane foam. In a specific embodiment the absorbent material 214 is in the form of a foam plug.

The device 200 can achieve disinfection when used on luer connectors by integrating disinfectant or antimicrobial agent in the chamber 212 of the cap 202. The disinfectant or antimicrobial agent can be directly included in the chamber 212 or disinfectant or antimicrobial agent can be absorbed into sponges or foam material that fills the chamber 212 of the cap 202. The device 200 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 214 toward the closed end 206 of the chamber 212 upon connection to the female luer connector or the male luer connector allows the connector to contact the disinfectant or antimicrobial agent to disinfect the female luer connector or the male luer connector.

In one or embodiments, the peelable seal 250 may be placed on the end face 216 to prevent the disinfectant or the antimicrobial agent from exiting the chamber 212.

In one or more embodiments, the peelable seal 250 comprises an aluminum or multi-layer polymer film peel back top. In a specific embodiment, the peelable seal 250 is heat-sealed or induction sealed to the cap open end. In one or more embodiments, the peelable seal 250 comprises a moisture barrier.

Referring to FIGS. 8 to 11, in one or more embodiments, the cap of the device of the present disclosure forms a fluid-tight seal with a female luer connector 300, male luer connector 400 or hemodialysis connector 500. Referring to FIGS. 8 to 11, in one or more embodiments, the cap of the device of the present disclosure is tapered to form a fluid-tight seal with a female luer connector 300 or male luer connector 400. In specific embodiments, the cap is compliant with ISO standards (e.g., ISO 594-1:1986 and ISO 594-2:1998) for forming a seal with a male luer connector 400.

In one or more embodiments, the cap of the device of the present disclosure has threads that have a size and pitch to engage a threadable segment of a female connector, such as for example, a female luer connector. Such connectors are generally and commonly used as catheter and other fluid-tight protective connectors in medical applications. In some embodiments, the cap provides a protective cover for a female luer connector when engaged with the connector when threads from the female luer connector engage and form a releasable connection with threads of the cap.

In some embodiments, the connector comprises a needleless injection site, which may sometimes be referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). In some embodiments, the cap can be connected with any of a variety of different needleless injection sites, such as those previously listed. In one or more embodiments, after the cap has been coupled with connector, it is unnecessary to disinfect (e.g. treat with an alcohol swab) the connector prior to each reconnection of the connector with another connector, as the connector will be kept in an uncontaminated state while coupled with the cap. Use of the cap replaces the standard swabbing protocol for cleaning connectors.

In one or more embodiments, threads of the cap are sized and pitched to engage threads of a male luer-lock connector. For example, connector can comprise the end of an IV tubing set that is disconnected from an IV catheter needleless injection site.

Other aspects of the present disclosure are directed to methods of disinfecting medical connectors and assemblies. In one or more embodiments, a method of disinfecting a medical connector comprises connecting the device of one or more embodiments to a medical connector, wherein connecting includes frictionally engaging the interior wall surface upon insertion into the chamber such that the medical connector contacts the absorbent material and the disinfectant or antimicrobial agent.

In one or more embodiments, an assembly comprises the device of one or more embodiments connected to a medical connector. In one or more embodiments, the medical connector is selected from a male luer connector, a female luer connector, and needleless connector.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A device for connection to a medical connector, the device comprising:

a cap comprising an integral body, a closed end, an annular wall having a length LC extending from the closed end to an open end and defining a chamber, the open end defining an end face, the open end defining an engagement surface, the chamber comprises a first portion adjacent the closed end having a first portion inner diameter and a second portion adjacent the open end having a second portion inner diameter, the first portion and second portion in fluid communication with each other and the first portion inner diameter being less than the second portion inner diameter, the first portion containing an absorbent material and disinfectant or antimicrobial agent;

the annular wall having an exterior wall surface and an interior wall surface;

a peripheral ledge extending radially between the interior wall surface of the second portion to the interior wall surface of the first portion;

an elastic sealing ring having a top surface and a bottom surface, the bottom surface disposed on the peripheral ledge, the elastic sealing ring extending radially inward from the interior wall surface, the elastic sealing ring having a dilatable opening therethrough sized and adapted to receive a male luer connector, a female luer connector and a hemodialysis connector, the dilatable opening sized to frictionally engage a male luer connector, wherein the peripheral ledge is disposed within the chamber and configured such that the male luer connector rests on the peripheral ledge upon being fully inserted in the chamber;

the interior wall surface comprising internal threads adjacent to the closed end, the internal threads disposed adjacent the closed end and partially extend from the closed end to the peripheral ledge, the internal threads positioned within the chamber and sized to engage a female luer connector, wherein when a male luer connector, a female luer connector and a hemodialysis connector is inserted through the dilatable opening, the absorbent material and the disinfectant or the antimicrobial agent contact the male luer connector, a female luer connector and a hemodialysis connector; and a peelable seal on the end face to prevent the disinfectant or the antimicrobial agent from exiting the chamber.

2. The device of claim 1, wherein the female luer connector is selected from the group consisting of needle-free connectors, catheter luer connectors, stopcocks, and hemodialysis connectors.

3. The device of claim 1, wherein the male connector is an intravenous tubing end, stopcock or male lock luer.

4. The device of claim 1, wherein the dilatable opening has a diameter that is dilatable from an initial diameter in a range from about 7-9 mm to a dilated diameter in a range from about 9-12 mm.

5. The device of claim 1, wherein the male luer connector frictionally engages the dilatable opening via a press-fit connection upon insertion into the chamber.

6. The device of claim 1, wherein the open end of the interior wall surface is sized and adapted to receive the elastic sealing ring in a press-fit connection.

7. The device of claim 1, wherein the elastic sealing ring comprises an elastomeric material.

8. The device of claim 1, wherein the annular wall of the cap is frusto-conically shaped.

9. The device of claim 1, wherein the exterior wall surface includes a plurality of grip members.

10. The device of claim 1, wherein the absorbent material compresses toward the closed end of the chamber upon connection to the female luer connector or the male luer connector.

11. The device of claim 10, wherein compression of the absorbent material disinfects the female luer connector or the male luer connector.

12. The device of claim 1, wherein the absorbent material is under radial compression by the internal threads to retain the absorbent material in the chamber.

13. The device of claim 1, wherein the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

14. The device of claim 1 wherein the elastic sealing ring has one or more undercuts on the surface of the elastic sealing ring facing the peripheral ledge.

15. The device of claim 1, wherein the elastic sealing ring has one or more undercuts and/or tapered surfaces disposed on the surface of the elastic sealing ring facing the dilatable opening.

16. The device of claim 1, wherein the elastic sealing ring has one or more undercuts and/or tapered surfaces disposed on the surface of the elastic sealing ring facing the dilatable opening and on the surface of the elastic sealing ring facing the peripheral ledge.

17. The device of claim 1, wherein the elastic sealing ring extends between the peripheral ledge and the open end.

18. The device of claim 1, wherein the elastic sealing ring extends from the peripheral ledge to the open end.

19. The device of claim 1, wherein an initial diameter of the dilatable opening of the elastic sealing ring is at least as large as the first portion diameter.

20. The device of claim 1, wherein the elastic sealing ring is disposed completely within the second portion.

* * * * *